United States Patent [19]

Fell et al.

[11] 4,188,363
[45] Feb. 12, 1980

[54] RECOVERY OF RHODIUM COMPLEX CATALYSTS HOMOGENEOUSLY DISSOLVED IN ORGANIC MEDIA

[75] Inventors: Bernard Fell, Aachen; Wilfried Dolkemeyer, Bornheim Uedorf, both of Fed. Rep. of Germany

[73] Assignee: Bayer Aktiengesellschaft, Leverkusen, Fed. Rep. of Germany

[21] Appl. No.: 953,339

[22] Filed: Oct. 20, 1978

Related U.S. Application Data

[63] Continuation of Ser. No. 823,231, Aug. 9, 1977, abandoned.

[30] Foreign Application Priority Data

Aug. 19, 1976 [DE] Fed. Rep. of Germany ....... 2637262

[51] Int. Cl.$^2$ .............................................. C01G 55/00
[52] U.S. Cl. ................... 423/22; 252/411 R; 252/413; 252/416
[58] Field of Search .................. 423/22; 252/411, 413, 252/416

[56] References Cited

U.S. PATENT DOCUMENTS

| | | | |
|---|---|---|---|
| 2,830,877 | 4/1958 | Appell | 423/22 |
| 3,071,551 | 1/1963 | Robinson et al. | 423/411 |
| 3,947,543 | 3/1976 | Thiel et al. | 252/413 |

FOREIGN PATENT DOCUMENTS

| | | | |
|---|---|---|---|
| 1588014 | 4/1970 | France | 423/22 |
| 45-1545 | 1/1970 | Japan | 423/22 |
| 1280707 | 7/1972 | United Kingdom | 423/22 |

*Primary Examiner*—Herbert T. Carter
*Attorney, Agent, or Firm*—Sprung, Felfe, Horn, Lynch & Kramer

[57] ABSTRACT

A process for the separation of rhodium catalysts from high-boiling and tarry distillation residues obtained in the processing of reaction products from organic, catalytic reactions, utilizing dissolved, homogenous rhodium complex catalysts, such as hydroformylation reactions, hydrocarboxylation reactions, isomerization, dimerization and oligomerization reactions, by passing a stream of a non-oxidizing, and preferably reducing, carrier gas, such as hydrogen or a hydrogen-containing gas, through the residue at an elevated temperature to selectively remove the organic constituents, leaving a heterogenous residue containing the rhodium, and dissolving this heterogenous residue in an inorganic acid to thereby form a water-soluble rhodium compound, which is suitable for the production of a complex rhodium catalyst in the known manner. Oleum is preferably used as the inorganic acid, and after mixing with the heterogenous residue, a portion is preferably fumed off.

9 Claims, 1 Drawing Figure

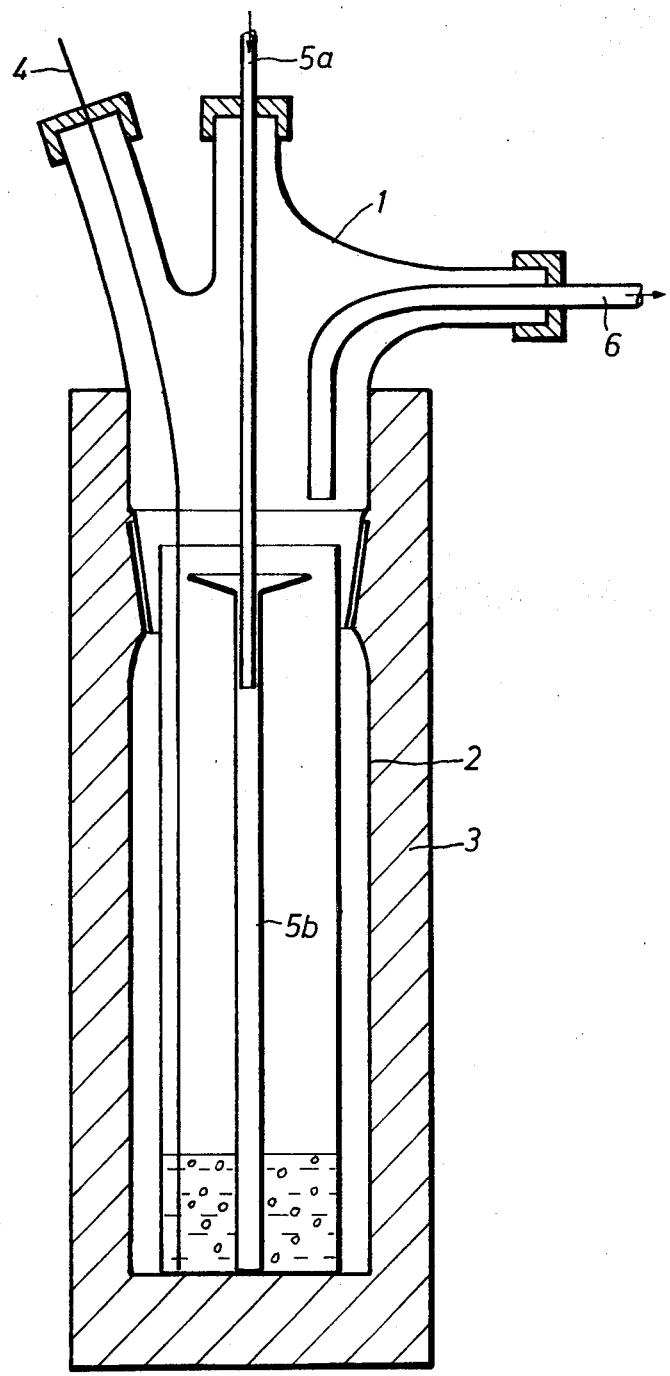

RECOVERY OF RHODIUM COMPLEX CATALYSTS HOMOGENEOUSLY DISSOLVED IN ORGANIC MEDIA

This is a continuation of application Ser. No. 823,231 filed Aug. 9, 1977, now abandoned.

The invention relates to a process for the recovery of rhodium complex catalysts homogeneously dissolved in organic compounds.

Numerous processes are known in which complex compounds of rhodium which are soluble in organic media are employed as homogeneous catalysts. For example, aldehydes and primary alcohols are prepared by reacting olefines with water gas (hydroformylation; H. Falbe, Carbon Monoxide in Organic Synthesis, 1st edition pp. 1–123, New York (1970)). Further examples of reactions of this type are the synthesis of dialcohols and dialdehydes (bishydroformylation) by reacting dienes with water gas (German Offenlegungsschrift (German Published Specification) No. 2,317,625) as well as the hydrocarboxylation of olefines using carbon monoxide and water or alcohols.

Rhodium complexes can also be employed in hydrogenation, double bond isomerisation, dimerisation and oligomerisation reactions. (C. W. Bird, Transition Metal Intermediates in Organic Synthesis, 1st edition pp. 30, 69 and 248, London (1967)).

After the reaction has ended and the reaction product has been separated off, in most cases by distillation, the rhodium complexes, which are chemically relatively stable, remain dissolved in a residue with which they can be recycled again into the reactor without a noticeable reduction in the catalytic activity.

In all these reactions high-molecular by-products which cannot be distilled form to a varying degree. In order to prevent their accumulation in the recirculated catalyst circuit, part of this stream must be withdrawn from the process. The valuable noble metal must be separated from the distillation residue in order to recycle it quantitatively as the catalyst into the process after any further working-up steps which may be necessary.

According to German Patent Specification No. 953,605, the complex, homogeneously dissolved rhodium catalyst can be decomposed to metallic rhodium which can then be recovered by filtration. This process has not proved economical because of the low yield of noble metal recovered and an expensive working-up to give a complex which is soluble in an organic medium.

In German Offenlegungsschrift (German Published Specification) No. 2,438,847 it is proposed to burn the organic solution containing the complex with oxygen and to absorb the noble metal particles, carried off in the off-gas stream, in an aqueous solution, it being possible to recover the phosphorus portion of the complex ligands in the form of phosphoric acid. Losses, which cannot be prevented even by optimising the process, also result in this case, so that application in industry cannot be considered.

Furthermore, according to U.S. Pat. No. 3,899,442, the rhodium homogeneously dissolved in the residue is precipitated under oxidising conditions onto an inorganic carrier which is then in each case employed again as a heterogeneous contact catalyst in the homogeneously catalysed reaction. Not inconsiderable losses result in this case through dusting of the inorganic carrier, which proves to be mechanically unstable at the high operating temperatures.

In addition, the transportation of the heterogeneous contact catalyst into the high pressure reaction chamber presents considerable difficulties.

According to a further German Offenlegungsschrift (German Published Specification) No. 2,311,388, the homogeneously dissolved rhodium catalyst is retained by adsorption onto magnesium silicate and elution of the entire heavy oil residue. The noble metal compound is subsequently quantitatively washed out of the sorption column. The extremely high consumption of expensive solvents makes this process appear unsuitable for large-scale industrial application.

A process for completely separating off and recovering rhodium catalysts from high-boiling or tarry distillation residues of organic reaction products has now been found, which is characterised in that a stream of carrier gas, with which the organic constituents are virtually completely carried off, is passed through the solution containing the rhodium catalyst at high temperatures and under normal or increased pressure, the heterogeneous residue containing rhodium in large concentrations is dissolved in an inorganic acid and the water-soluble rhodium compound thereby formed is worked up in a manner which is in itself known or directly employed as the catalyst in a hydroformylation reaction.

In detail, the process according to the invention is carried out as follows:

A homogeneous solution consisting of a rhodium complex and a high-boiling distillation residue is heated in a reaction vessel through which a stream of carrier gas continuously flows. The vessel is described with the aid of the diagram, the numbers of which have the following meaning: (1) upper part of glass reactor; (2) lower part of glass reactor; (3) heating; (4) thermocouple; (5a) metal capillary, glass inlet; (5b) glass capillary; and (6) product outlet. All the constituents of the heavy oil as well as all the products formed by the pyrolysis reaction are carried off with the gas. The noble metal remains in the reaction chamber in a high concentration.

The heterogeneous residue is dissolved in the reaction vessel with an inorganic acid and converted into a form which is soluble in an aqueous medium.

The conversion of the water-soluble rhodium compound into a complex which is soluble in an organic medium is carried out in a manner which is in itself known under the reaction conditions which are also customary for hydroformylation.

The rhodium catalysts which can be recovered by the process according to the invention are compounds which are soluble in an organic medium to give a homogeneous solution. Ligands on the central rhodium atom can be phosphines or phosphites which contain, as organic radicals, aliphatic and/or aromatic, preferably benzene-type, hydrocarbon radicals. In addition to the phosphines and phosphites, the complexes can also contain further ligands, such as, for example, hydrogen atoms, halogen atoms, nitrogen atoms, arsenic atoms, antimony atoms, tin atoms, silicon atoms, carbonyl radicals, carboxylate groups, acetylacetonate groups or cyclopentadienyl radicals.

Examples of complex rhodium catalysts which may be mentioned are: hydridocarbonyl-tris(triphenylphosphine)-rhodium (I), carbonyl-(tributylphosphine)acetylacetonatorhodium-(I), carbonyl-(triphenylphosphine)3-ethylacetyl-acetonatorhodium-(I), hydridocarbonyl-tris-(triarylphosphine)-rhodium-(I), hydridocarbonyl-tris-(triphenylphosphite)-rhodium-(I), bis-(triaryl-phosphine)-rhodium carbonyl chloride, bis-(tributylphosphine)-carbonyl-rhodium-(I), hydridocarbonyl-tris(tribenzylamine)-rhodium-(I) and other amine complexes, rhodium carbonyl/phosphine/biphosphanes, rhodium carbonyl/As or Sb compounds and rhodium carbonyl/Sn compounds.

In general, the high-boiling distillation residues which are separated, according to the invention, from the noble metal are polycondensation and polymerisation products which are formed, for example, by secondary reactions and side reactions during the hydroformylation or hydrocarboxylation. They essentially contain aldols, unsaturated aldehydes, unsaturated ethers, ether-aldehydes and ether-alcohols, cyclic ethers, esters and organic acids.

Non-oxidising gases are employed as the carrier gas. Examples of suitable gases are nitrogen, methane, ethane, hydrogen, water gas and synthesis gas. Hydrogen or a gas mixture containing hydrogen is particularly preferred. A decomposition of the tertiary phosphine or tertiary amine ligands which are present in most cases in excess in the mixture employed is thereby avoided. In addition, in this case no rhodium oxide, which is difficult to work up, is formed. By employing a reducing carrier gas, which is preferably used, for example hydrogen or a gas containing hydrogen, the rhodium is obtained in a very active form rich in hydrogen and thus dissolves relatively easily in inorganic acids. The flow rate of the gas is of minor importance for the inventive process. Preferably a flow rate of 0.2 to 2.0 l/min (STP) is employed. Suitable inorganic acids are: hydrochloric acid, hydrobromic acid, nitric acid, sulphuric acid and oleum. In general, the acid is added in the concentrated form.

Preferably, concentrated sulphuric acid and 10-50% strength oleum are used.

15-20% strength oleum is particularly preferred.

The heating of the solution in the flow system can be carried out under a static pressure of 1-300 bars. Suitable temperatures are from about 100°-600° C., preferably 250° to 350° C. Under the reaction conditions, the heavy oil is converted by pyrolysis reactions into low-boiling products which can be transported out of the system with the stream of carrier gas by distillation. Saturated and unsaturated hydrocarbons of low C numbers are formed as products in a procedure using increased static pressure. If the reaction is carried out under normal pressure, a proportion of the heavy oil is carried off undecomposed with the carrier gas. If complex ligands are present in excess in the mixture employed, as a rule, surprisingly, they do not influence the separation of noble metal and heavy oil. They are carried off with the stream of carrier gas and can, if appropriate, be recovered relatively easily from the distillate for reemployment. Not even traces of rhodium are expelled in the process according to the invention.

Strongly oxidising inorganic acids are preferably employed for dissolving the residues containing rhodium. The reaction is particularly preferably carried out with concentrated sulphuric acid or oleum.

The conversion of the rhodium dissolved in the acid into a complex compound which is soluble in organic media is then carried out in a manner which is in itself known. The rhodium compound present in the aqueous solution can also be directly recycled into the reactor as a catalyst, for example for the hydroformylation.

It is particularly advantageous to carry out the separation of the rhodium by the procedure of the invention discontinuously.

An advantage of the process according to the invention is that the rhodium catalyst can be recirculated quantitatively and without loss in activity into the catalyst/solvent circuit. In comparison with some known processes, obtaining the noble metal in such a form that it can only be worked up for reemployment with considerable difficulties and losses is avoided. The separation procedure by the process of the invention is carried out with a very low expenditure on apparatus. Losses of rhodium do not occur.

In the examples which follow, the percentage data are percentages by weight.

EXAMPLE 1

500 g of n-valeraldehyde are heated to 300° C. for 72 hours in a piston-stirred autocalve. The low-boiling polycondensation products are then distilled off under a high vacuum. 300 mg of HRhCO (PPh$_3$)$_3$ together with 1,200 mg of PPh$_3$ are dissolved in 15 g of the residue, which cannot be distilled, at about 100° C., whilst adding hydrogen. A continuous stream of H$_2$ of 0.4 l/minute is passed through the mixture in the reaction vessel in the diagram. After its exit from the reaction chamber, the gas stream is passed through two wash bottles, connected in series, containing the above polycondensation products and toluene as the absorption liquid. The reactor is heated to 300° C. for 90 minutes and subsequently cooled. 169 mg of solid residue remain in the reaction chamber. No rhodium can be detected in either of the two wash bottles. Thus the entire noble metal constituent remains in the solid residue.

15 g of oleum (10 percent strength) are filled into the reaction vessel and 25% of this oleum is evaporated off as fumes at about 300° C. The off-gases are withdrawn under a slight vacuum and passed through a wash bottle containing H$_2$O as the absorption liquid. It is also not possible to detect rhodium in the water. The residual acid, containing noble metal, is diluted with 162 ml of H$_2$O to give a 7 percent strength sulphuric acid. The solution is coloured dark brown. The entire amount of rhodium employed is detected in the solution.

EXAMPLE 2

400 ml of heptanal are kept at the boil with 100 ml of toluene and 50 g of the ion exchanger Lewatit 500 M (—N(CH$_3$)$_3$ particle size 1.2 mm) for 48 hours. The ion exchanger is filtered off and the product is subsequently concentrated to the so-called heavy oil by vacuum distillation. 12 g of this heavy oil are put into the reaction vessel together with 300 mg of HRhCO (PPh$_3$)$_3$ and 1,200 mg of PPh$_3$, under a stream of hydrogen of 0.4 l/minute.

The homogeneous solution obtained after increasing the temperature to 100° C. is subsequently heated to 300° C. After its exit from the reaction vessel, the continuous stream of hydrogen which bubbles through the solution is passed through a wash bottle containing toluene as the absorption liquid. All the heavy oil constituents are carried off with the gas stream at 300° C. in the course of 60 minutes. A solid residue of 186 mg, in which the rhodium constituent employed is contained to an extent of 100%, remains in the reaction vessel.

11 g of oleum are filled into the reaction vessel, which is heated to 300° C. for about 1 hour. The reaction mixture is taken up in 136 g of H₂O. The solution is coloured dark brown and contains the entire rhodium.

The aqueous solution, together with 57 ml of toluene and 1.2 g of PPh₃, is put into a 500 ml piston-stirred autoclave under a water gas atmosphere of 240 bars with a partial pressure ratio $P_{H_2}/P_{CO}=0.55$ for three hours at a temperature of 120° C. After the experiment has ended, the aqueous phase is free from rhodium.

The catalyst complex recovered is employed, without loss in activity, in the isomerisation-free hydroformylation of but-2-ene.

EXAMPLE 3

17 g of the residue, which cannot be distilled, from Example 1 are employed, together with 300 mg of HRhCO (PPh₃)₃ and 1,200 mg of PPh₃, in the same experimental arrangement and under the same conditions as in Example 1, except that the gas throughput is increased from 0.4 to 0.7 l/minute (STP) and that the gas pressure is increased from 1 to 20 bar. 225 mg of a solid residue already remain in the reactor after a duration of the experiment of 40 minutes. No detectable amounts of rhodium are carried off in the gas stream.

26.4 g of oleum are filled into the reactor and the residue is treated with the acid at room temperature. After diluting with 200 ml of H₂O, an aqueous, deep black solution is obtained, from which small black particles slowly precipitate. Only 47% of the rhodium employed are homogeneously dissolved. 53% of the noble metal remain as an insoluble compound in the suspension. Thus, treatment of the rhodium residue at a higher temperature is necessary for complete recovery.

EXAMPLE 4

16.7 g of the residue, which cannot be distilled, from Example 1 are employed, together with 300 mg of HRhCO (PPh₃)₃ and 1,200 mg of PPh₃, in the same experimental arrangement and under the same conditions as in Examples 1 and 2. Nitrogen is used as the carrier gas. The gas throughput is 0.4 l/minute. 234 mg of a heterogeneous residue remain in the reactor after a duration of the experiment of 60 minutes. No detectable amounts of rhodium are carried off from the reaction vessel in the gas stream and the liquid.

16.4 g of oleum are filled into the reaction vessel, and 28% of this oleum are expelled when heated. In this case also, no rhodium is carried off. The residual acid containing noble metal is diluted with 203 ml of H₂O to give a 6% strength sulphuric acid. Solid particles settle out of the medium-brown solution. 82% of the rhodium employed are homogeneously dissolved. 18% of the noble metal remain in the sediment as a compound which is insoluble under these conditions. This shows that the use of a gas containing hydrogen is necessary in the cracking of residues containing rhodium in order to regenerate the noble metal completely.

What is claimed is:

1. A process for the separation of rhodium catalysts, having as ligands on the central rhodium atom a phosphine or phosphite which contains aliphatic and/or aromatic hydrocarbon radicals, from high-boiling and tarry distillation residues obtained in the processing of reaction products from organic catalytic reactions utilizing dissolved homogenous rhodium complex catalysts, which consists of passing a stream of hydrogen or a hydrogen-containing gas through the residue at an elevated temperature of between 100°–660° C. to thereby selectively remove the organic constituents, leaving a heterogenous solid residue containing the rhodium, and thereafter dissolving the heterogenous residue in an inorganic acid selected from the group consisting of hydrochloric acid, hydrobromic acid, nitric acid, sulphuric acid and oleum to thereby form a water-soluble rhodium compound suitable for the production of a complex rhodium catalyst.

2. Process according to claim 1, in which said carrier gas is a hydrogen-containing gas.

3. Process according to claim 2, in which said carrier gas is hydrogen.

4. Process according to claim 1, in which said inorganic acid is oleum.

5. Process according to claim 4, in which, after the oleum is added to the heterogenous residue, a portion of the oleum is evaporated off as fumes.

6. Process according to claim 1, in which the hydrogen or a hydrogen-containing gas is passed through the residue while maintaining the residue at an elevated temperature of about 250°–350° C.

7. Process according to claim 1, in which the hydrogen or a hydrogen-containing gas is passed through the residue at ambient pressure.

8. Process according to claim 1, in which the hydrogen or a hydrogen-containing gas is passed through the residue at an elevated pressure of up to 300 bars.

9. Process according to claim 8, in which the hydrogen or a hydrogen-containing gas is passed through the residue at an elevated pressure of between 2–100 bars.

* * * * *

UNITED STATES PATENT AND TRADEMARK OFFICE
CERTIFICATE OF CORRECTION

PATENT NO. : 4,188,363
DATED : February 12, 1980
INVENTOR(S) : Bernard Fell, et al.

It is certified that error appears in the above-identified patent and that said Letters Patent are hereby corrected as shown below:

On Title page, [73] Assignee: delete "BAYER AKTIENGESELLSCHAFT, Leverkusen, Fed. Rep. of Germany" and substitute --Erdolchemie GmbH, Koeln, Germany--.

Signed and Sealed this

Second Day of December 1980

[SEAL]

Attest:

SIDNEY A. DIAMOND

Attesting Officer

Commissioner of Patents and Trademarks